(12) United States Patent
Ropella et al.

(10) Patent No.: US 10,247,791 B2
(45) Date of Patent: Apr. 2, 2019

(54) SYSTEM FOR CONVERTING AUDIO SIGNALS TO WIRELESS AUDIO SIGNALS IN A MEDICAL IMAGING ENVIRONMENT

(71) Applicant: Neocoil, LLC, Pewaukee, WI (US)

(72) Inventors: Paul Ropella, New Berlin, WI (US); Brian Brown, Wauwatosa, WI (US); Michael Naughton, Oconomowoc, WI (US); Liang-Sywan Edward Jen, Glendale, WI (US)

(73) Assignee: NeoCoil, LLC, Pewaukee, WI (US)

( * ) Notice: Subject to any disclaimer, the term of this patent is extended or adjusted under 35 U.S.C. 154(b) by 0 days.

(21) Appl. No.: 15/803,105

(22) Filed: Nov. 3, 2017

(65) Prior Publication Data

US 2018/0128888 A1   May 10, 2018

Related U.S. Application Data (60) Provisional application No. 62/417,664, filed on Nov. 4, 2016.

(51) Int. Cl.
*G01R 33/28* (2006.01)
*A61B 5/055* (2006.01)
*H04R 1/10* (2006.01)

(52) U.S. Cl.
CPC .......... *G01R 33/283* (2013.01); *A61B 5/055* (2013.01); *H04R 1/1033* (2013.01); *H04R 1/1083* (2013.01)

(58) Field of Classification Search
CPC .... G01R 33/283; A61B 5/055; H04R 1/1033; H04R 1/1083
See application file for complete search history.

(56) References Cited

U.S. PATENT DOCUMENTS

| | | | | |
|---|---|---|---|---|
| 5,277,184 A | * | 1/1994 | Messana | A61B 5/055 324/318 |
| 5,313,945 A | * | 5/1994 | Friedlander | G01R 33/3854 324/318 |
| 5,627,902 A | * | 5/1997 | Ziarati | G01R 33/283 181/129 |
| 6,463,316 B1 | * | 10/2002 | Brungart | A61B 5/055 381/71.1 |
| 9,244,139 B2 | | 1/2016 | Brown et al. | |
| 9,264,793 B2 | | 2/2016 | Brown et al. | |
| 9,438,981 B2 | | 9/2016 | Brown et al. | |
| 2005/0111687 A1 | * | 5/2005 | Lederer | G01R 33/283 381/380 |

(Continued)

*Primary Examiner* — Tuan D Nguyen
(74) *Attorney, Agent, or Firm* — Boyle Fredrickson, SC (57) ABSTRACT

An improved system for providing audio signals to a patient during medical imaging is disclosed. A converter device is operatively connected to a audio signal transmitter such as a pneumatic audio port commonly used for pneumatic headphones. The converter device includes a connecting member removably inserted into the pneumatic audio port. A microphone receives the pneumatic audio signals and converts these signals to electronic audio signals. The converter device further includes a wireless transmitter that converts the electronic audio signals to wireless signals and transmits the wireless signals to a wireless receiver. The wireless receiver may be located in a headset worn by the patient, which receives the wireless signals and provides the audio content to the patient during imaging.

19 Claims, 9 Drawing Sheets

(56) References Cited

U.S. PATENT DOCUMENTS

2015/0100310 A1* 4/2015 Cha .................. G10L 21/0208
  704/228
2017/0086703 A1* 3/2017 Wirtz .................. A61B 5/0051
2017/0150247 A1* 5/2017 Smith .................. H04R 1/2876

* cited by examiner

SYSTEM FOR CONVERTING AUDIO SIGNALS TO WIRELESS AUDIO SIGNALS IN A MEDICAL IMAGING ENVIRONMENT

CROSS-REFERENCE TO RELATED APPLICATIONS

This application claims priority to U.S. provisional application Ser. No. 62/417,664, filed Nov. 4, 2016, the entire contents of which is incorporated herein by reference.

BACKGROUND OF THE INVENTION

The subject matter disclosed herein relates to a system for converting audio signals to wireless audio signals in a medical imaging environment. More specifically, a device may be operatively connected to an existing audio system for a magnetic resonance imaging (MRI) system to receive audio signals generated by the audio system and to convert the audio signals to wireless audio signals for delivery to a wireless headset worn by a patient on the scan table.

As is known to those skilled in the art, a magnetic resonance imaging (MRI) system alternately generates a strong magnetic field and then detects the faint nuclear magnetic resonance (NMR) signals given off by nuclei in the presence of the magnetic field. The NMR signals are received by antennas, also known as coils, and transmitted to the MRI scanner for reconstruction into an MRI image. In order to provide a clear image, it is desirable to minimize interference associated not only with external artifacts, such as electromagnetic interference, but also with motion artifacts, such as voluntary or physiologic motion.

During a MRI procedure, the MRI scanner generates a significant level of audible noise in the scanner's switching gradient coils. The rapid switching of the coils to generate the magnetic field in the scanner causes vibration in the coils. The vibration, in turn, generates audible noise. As the switching speed and strength of the gradient coils in the scanner increase, the magnitude of noise increases as well. The magnitude of noise in an MRI scanner is sufficient that communication with a patient during the MRI procedure becomes difficult. Typically, headsets are provided such that audio signals containing instructions or information from a technician performing the procedure to be delivered directly to the patient's ear. Further, the headsets may include some level of noise protection to reduce the level of ambient noise generated by the MRI scanner from reaching the patient's ear.

The MRI environment creates numerous challenges that make conventional electronic headsets unusable in the MRI environment. Most commercial headsets utilize a magnetic speaker driver and may include one or more other components that are susceptible to magnetic fields. The magnetic field generated by the MRI scanner may, at a minimum, interfere with these devices, and at worst, pull the devices into the bore of the scanner, potentially injuring the patient. Further, non-magnetic metal components may be susceptible to radio frequency (RF) induced heating. Also, long wire runs, for example, between the control room and the patient or even between earphones function as antennas. These long wire runs raise the potential of both radiating electromagnetic interference detectable by the MRI scanner due to audio signals transmitted on the wire and receiving interference from the MRI scanner which degrades the audio signal provided to the patient.

Historically, these limitations of conventional electronic headsets have been overcome by providing pneumatic headsets to the patient. However, such a system is not without drawbacks. The pneumatic headsets require a dedicated controller with a speaker to convert an electronic audio signal to an audile audio signal proximate a first end of a pneumatic tube. The pneumatic tube, in turn, acts as a conduit for transmitting the audible audio signal to the patient. Pneumatic tubing extending from this controller o the patient is also required.

On some scanners, the controller is provided on the scanner or within the scan table. The pneumatic tubing must extend from the controller to the patient. The scan table typically includes a sliding top such that the patient may initially get on the table and be oriented by a technician on the table top external to the MRI scanner. The top then slides into the bore of the MRI scanner to perform the imaging. The pneumatic tubing must be provided with sufficient length to plug into the table and allow the headphones to reach the length of the table and in some instances to also accommodate the travel of the table into and out of the bore of the MRI scanner.

With other scanners, no controller is provided and a separate controller must be provided within the scan room. Pneumatic tubing must be routed between the controller and the scanner. The tubing may be routed along the floor or within troughs embedded in the floor of the scan room. Tubing along the floor presents a trip hazard within the scan room and complicates work flow for other medical equipment that must be positioned within the scan room. Whether routed along the floor or within troughs, the length of the tubing increases if the controller is located remotely from the scanner.

Thus, it would be desirable to provide an improved system for providing the audio signals to the patient.

BRIEF DESCRIPTION OF THE INVENTION

The subject matter disclosed herein describes an improved system for providing audio signals to a patient during medical imaging. A converter device is operatively connected to an audio signal transmitter such as a pneumatic audio port commonly used for pneumatic headphones. The converter device includes a connecting member removably inserted into the pneumatic audio port. A microphone receives the audio signals traveling through the pneumatic system and converts these signals to electronic audio signals. The converter device further includes a radio frequency (RF) wireless transmitter that converts the electronic audio signals to RF wireless signals and transmits the wireless signals to an RF wireless receiver. The RF wireless receiver may be located in a headset worn by the patient, which receives the wireless signals and provides the audio content to the patient during imaging.

According to one embodiment of the invention, an audio signal converter for use in a magnetic resonance imaging (TARO environment is disclosed. The audio signal converter includes a housing and a connecting member extending from the housing. The connecting member has an outer periphery that is complementary to a pneumatic audio port within the MRI environment, and the connecting member is operative to be inserted into the pneumatic audio port. The connecting member includes an opening at an end distal from the housing, and a passage extends through the connecting member from the opening to an interior of the housing. The audio signal converter also includes a microphone and a wireless transmitter. The microphone is mounted proximate the connecting member and is operative to receive a pneumatic audio signal via the passage in the connecting member and to convert the pneumatic audio signal to an electronic audio signal. The wireless transmitter is mounted within the housing and is operative to receive the electronic audio signal and to transmit a radio frequency (RF) audio signal to a receiver within the MRI environment. Each of the components of the audio signal converter has a low magnetic susceptibility such that the audio signal converter will not be drawn toward a magnetic field applied by an MRI scanner and will not distort the homogeneity of the magnetic field.

According to another aspect of the invention, the pneumatic audio port is located in a chamber on either the MRI scanner or a table for the MRI scanner, and the housing is configured to fit in the chamber on the MRI scanner or the table for the MRI scanner. The audio signal converter may also include an insert configured to be fitted within the passage of the connecting member. The insert includes a first end and a second end, where the first end is proximate the interior of the housing when the insert is fitted within the passage of the connecting member, and the insert includes a channel extending from the first end for at least a portion of a length of the insert. The microphone is configured to be positioned within the channel of the insert.

According to another aspect of the invention, the audio signal converter may include a gasket mounted to the outer periphery of the connecting member and operative to form a seal between the outer periphery of the connecting member and the pneumatic audio port when the connecting member is inserted into the pneumatic audio port. The housing may include at least two portions, and the audio signal converter may include a sealing member included between the two portions when the two portions are joined together to firm the housing.

According to still other aspects of the invention, the microphone may be a low sensitivity microphone. Optionally, the connecting member may be operative to be positioned proximate a speaker generating an audio signal for a patient in the MRI environment. The audio signal converter may include a rechargeable battery pack, where the rechargeable battery pack includes multiple batteries.

According to another embodiment of the invention, a method for converting pneumatic audio signals to radio frequency (RF) wireless signals in a magnetic resonance imaging (MRI) environment is disclosed. A connecting member of an audio signal converter is inserted into a pneumatic audio port located in the MRI environment, and an audio signal is received with a microphone in the audio signal converter from the pneumatic audio port via a passage extending through the connecting member in the audio signal converter. The audio signal is converted to an electronic audio signal with the microphone, and the electronic audio signal is converted to an RF wireless signal with a wireless transmitter mounted in the audio signal converter. Each of the components of the audio signal converter has a low magnetic susceptibility such that the audio signal converter will not be drawn toward a magnetic field applied by an MRI scanner and will not distort the homogeneity of the magnetic field.

According to another aspect of the invention, an ambient noise received at the microphone is attenuated, where the ambient noise is generated by operation of the MRI scanner. The audio signal converter includes an insert configured to be fit within the passage of the connecting member, and the insert includes a channel extending from a first end for at least a portion of a length of the insert. The microphone is configured to be positioned within the channel of the insert. The audio signal converter further includes a gasket mounted to the outer periphery of the connecting member, and the gasket is operative to form a seal between the outer periphery of the connecting member and the pneumatic audio port when the connecting member is inserted into the pneumatic audio port. The insert and the gasket are operative to attenuate the ambient noise generated by the MRI scanner.

According to still another embodiment of the invention, a system for delivering pneumatic audio signals to a patient in a magnetic resonance imaging (MRI) scanner is disclosed. The system includes a signal converter and a wireless audio delivery system. The signal converter includes a housing and a connecting member extending from the housing. The connecting member has an outer periphery that is complementary to a pneumatic audio port on either the MRI scanner or a table for the MRI scanner, and the connecting member is operative to be inserted into the pneumatic audio port. The connecting member includes an opening at an end distal from the housing, and a passage extends through the connecting member from the opening to an interior of the housing. A microphone is mounted proximate the connecting member and is operative to receive a pneumatic audio signal via the passage in the connecting member and to convert the pneumatic audio signal to an electronic audio signal. A wireless transmitter is mounted within the housing and is operative to receive the electronic audio signal and to transmit a radio frequency (RF) audio signal to a receiver within the MRI environment. The wireless audio delivery system includes the receiver and at least one speaker. The receiver is operative to receive the RF audio signal and to convert the RE audio signal to a second electronic audio signal within the wireless headset. The at least one speaker is operative to convert the second electronic audio signal to an audible audio signal proximate an ear of the patient. Each of the components of the signal converter and of the wireless headset has a low magnetic susceptibility such that the signal converter and the wireless headset will not be drawn toward a magnetic field applied by an MRI scanner and will not distort the homogeneity of the magnetic field.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

FIG, 10 is a sectional view of the pneumatic to wireless audio signal conversion device of FIG. 5 taken at 10-10 of FIG. 9.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements and/or wireless connection where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 1:
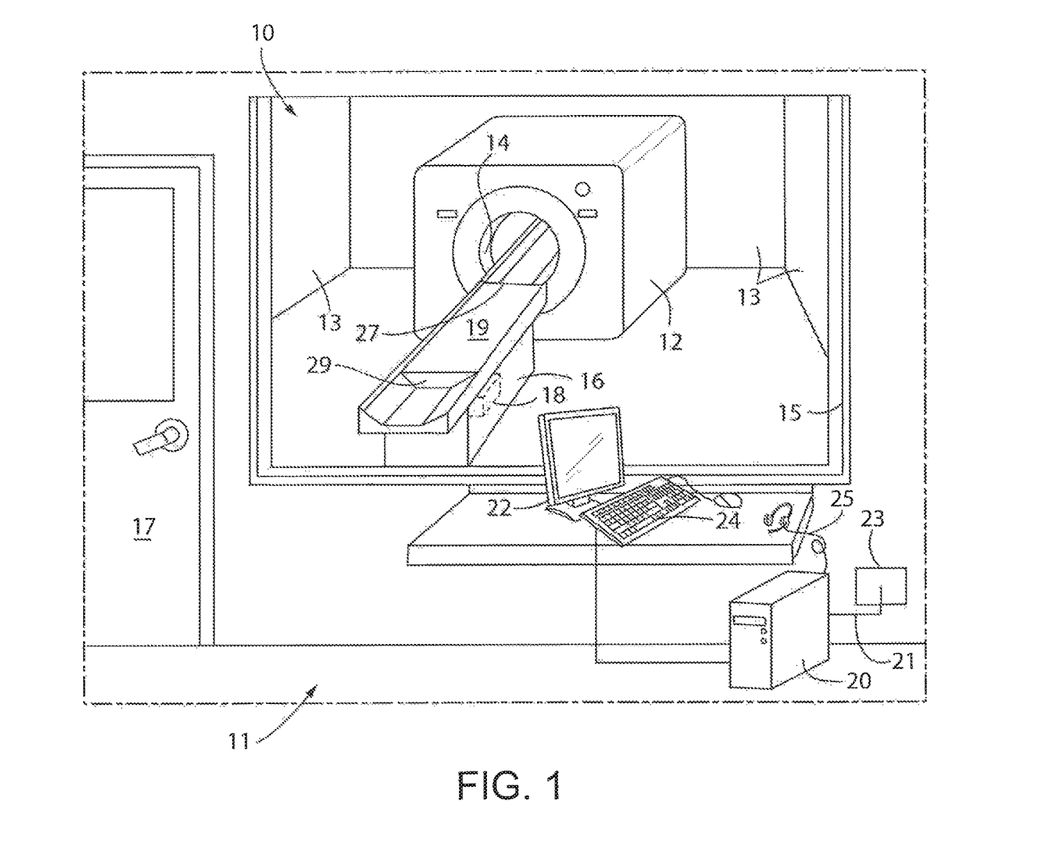
FIG. 1 is a exemplary embodiment of an MRI scan room.
Figure 2:
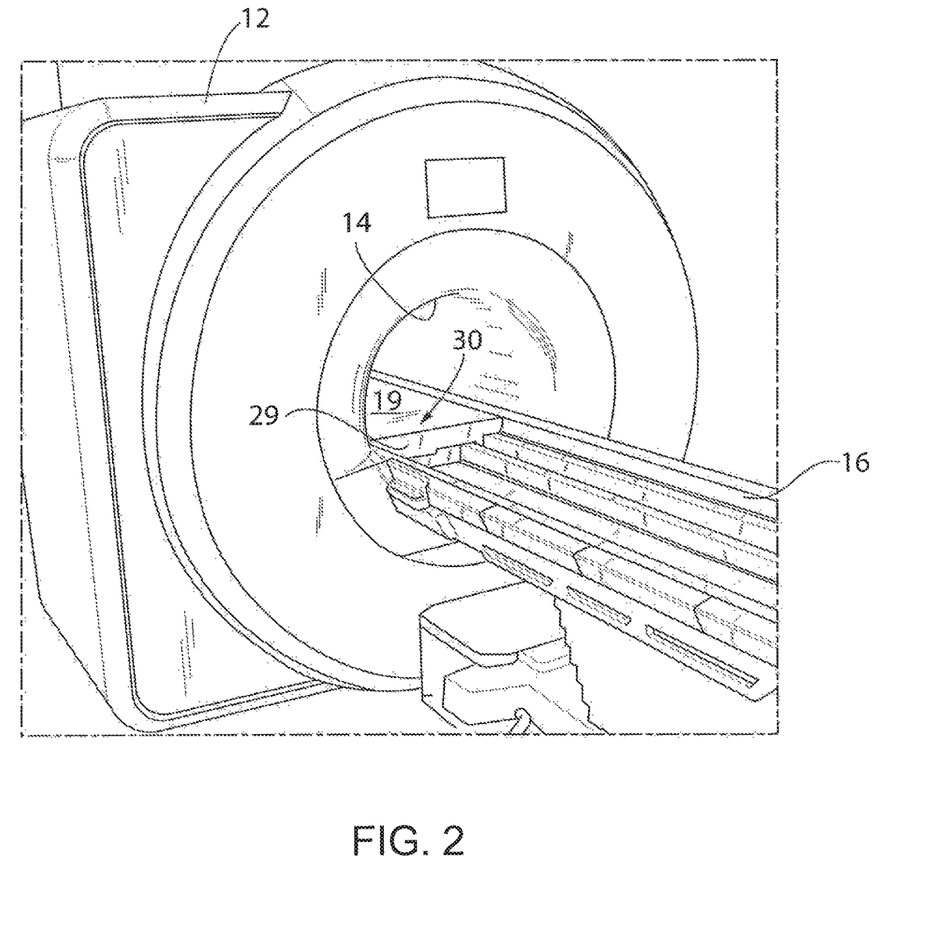
FIG. 2 is a pictorial view of an exemplary MRI scanner.

Referring initially to FIGS. 1.-2, an exemplary shielded room 10 containing an MRI scanner 12 is illustrated. The scan room 10 includes walls 13, or panels, which typically incorporate RF shielding within the wall 13. A window 15 permits an operator to observe activity within the scan room 10 from an adjacent control room 11, typically connected via a door 17. The door 17 may similarly incorporate RF shielding within the solid portion of the door. The window 15 between the scan room 10 and the control room 11 and, if present, a window in the door 17 are covered in a conductive material such as a fine wire mesh or a thin metallic foil made, for example, from copper or gold to provide RF shielding on the window. The shielding is configured to prevent external RF signals that are in a spectrum that may interfere with the MRI scanner 12 from entering the scan room 10 and causing said interference.

A controller 20 for the MRI scanner 12 is typically located in the adjacent control room 11. An operator interface including, for example, a monitor 22 or other display unit and an input device such as a keyboard 24 are connected to the controller 20. The controller 20 may be connected to the MRI scanner 12 by cabling extending, for example, under the floor of the scan room 10 or in a shielded conduit to the MRI scanner 12. A penetration panel 23 in the wall may also provide connections to cables 21 running from the controller 20 into the scan room 10. The penetration panel 23 may include connectors for cabling to other medical equipment present in the scan room 10. Corresponding connectors on the other side of the penetration panel 23 within the scan room 10 permit appropriately shielded cables to be connected and run to the scanner 12 or to other medical equipment.

It is further contemplated that control room 11 may be equipped to deliver audio signals to a patient in the scan room 10. The audio signals may include, for example, operator or automatically generated voice instructions or patient entertainment such as a music file. A headset 25 operatively connected to the controller 20 may be provided for the technician. The headset 25 may include earphones to receive voice signals from the patient and a microphone into which the technician may speak to provide instructions to the patient. The controller 20 may include an internal storage device, such as a hard drive, a solid-state drive, or the like on which a library of audio files, such as music files, may be stored. Optionally, the controller 20 may include a removable media drive, such as a CD drive, DVD drive, memory card reader, USB port, and the like to receive a removable medium on which one or more audio files are stored. According to still another embodiment, an external media player (not shown) may be connected to and provide audio content to the controller 20. The controller 20 may be operative to combine or prioritize each of the audio sources for delivery of audio content to the patient. For instance, audio content received from the microphone on the headset 25 may take priority over other sources and temporarily inhibit delivery of other content while the audio content from the technician is delivered to the patient. The controller 20 receives audio content from each of these sources and generates electronic audio signals for delivery into the scan room. The electronic audio content is delivered via the cables 21 through the penetration panel 23 into the scan room 10. Delivery of audio content, such as a music file, provides comfort to and relaxes the patient during the imaging procedure. The additional audio content provides an improved imaging experience and, with a more relaxed patient, reduces the likelihood of motion induced artifacts due to the patient moving, for example, from fidgeting or adjusting potion during the imaging procedure.

A receiver 18 within the scan room 10 receives the electronic audio content and processes the electronic audio content for delivery to a patient on the table 16. According to the illustrated embodiment, the receiver 18 is mounted within the table 16. Shielded cables may extend from the penetration panel 23 either along the floor or, preferably, in a cable trough recessed into the floor. The cable trough is covered to provide a level floor surface, thereby protecting the shielded cables from damage due to equipment rolling over or personnel stepping on the cables and enhancing safety by eliminating a trip hazard. The receiver 18 includes a speaker to convert the electronic audio signals from the controller 20 back into audible audio signals proximate a first end of pneumatic tubing for delivery to a patient. The pneumatic tubing acts as a conduit through which the audible audio signals travel. These audible audio signals traveling through the pneumatic tubing will be referred to herein as pneumatic audio signals. It is contemplated that the receiver 18 may be located external from the table 16 as well. For example, the receiver 18 may be located proximate the penetration panel 23 within the scan room 10 and have pneumatic tubing running along the floor or in the cable trough to the table 16 rather than a shielded cable.

In addition to providing pneumatic audio signals to the patient, the table 16 may utilize other pneumatic signals or devices to interact with the patient. For example, a vacuum cushion may be provided to provide stability for the patient. The vacuum cushion is located under the patient while initially loading the patient on the table 16, and a vacuum is generated to draw air out of the cushion. With the vacuum applied the cushion forms around the patient. The vacuum cushion provides support to and helps retain the patient in the same position during imaging. According to another example, a squeeze bulb may be provided to the patient where the patient may squeeze the bulb in response to a technician's question or to indicate discomfort. The air output from the bulb in response to being squeezed generates a pneumatic signal from the patient. A transducer mounted on the table may convert the airflow output from the bulb to an electric signal for delivery to the controller and to a technician performing a scan within the control room 11.

Figure 3:
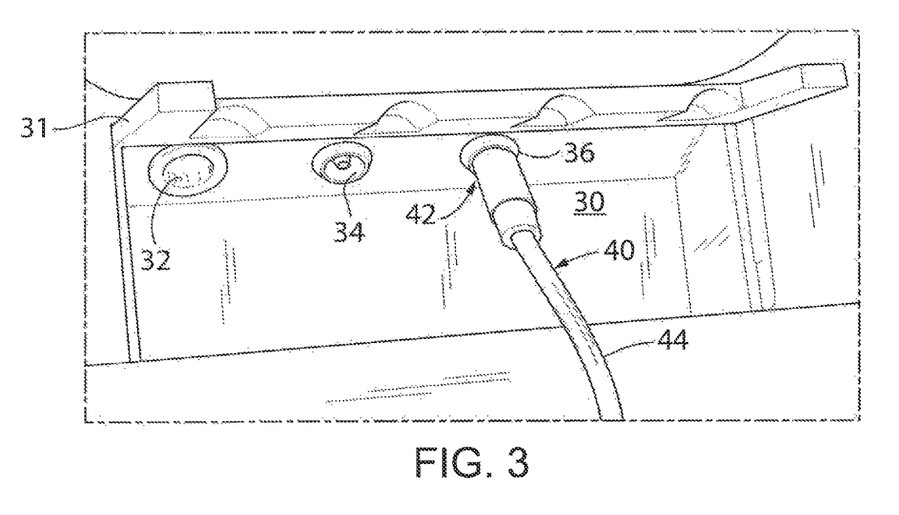
FIG. 3 is a pictorial view of a set of pneumatic ports on the scan table of the MRI scanner of FIG. 2 taken from the top.
Figure 4:
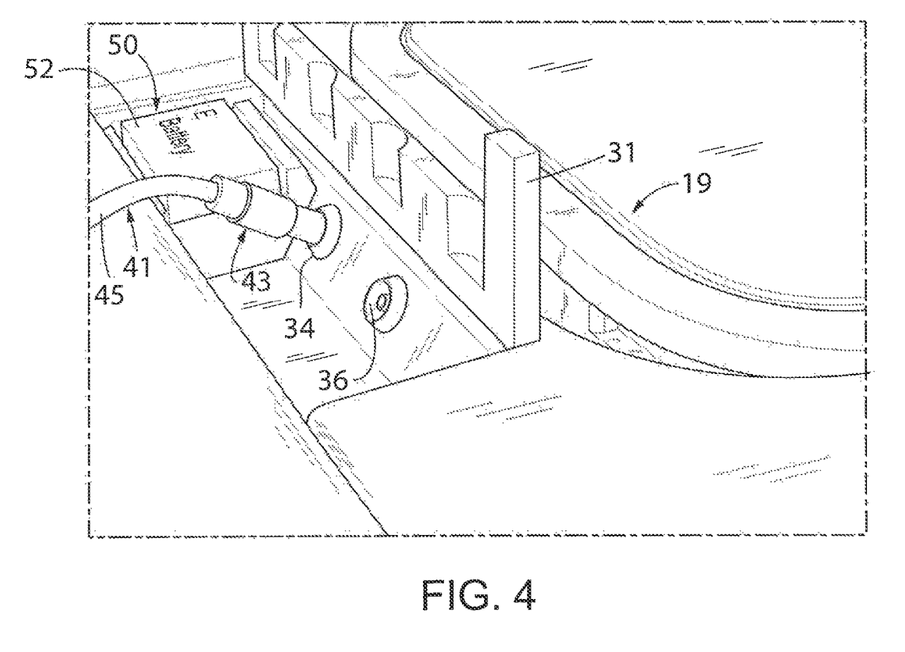
FIG. 4 is a pictorial view of the set of pneumatic ports on the scan table of the MRI scanner of FIG. 2 with one embodiment of a pneumatic to wireless audio signal conversion device connected taken from the top and right side.
Figure 5:
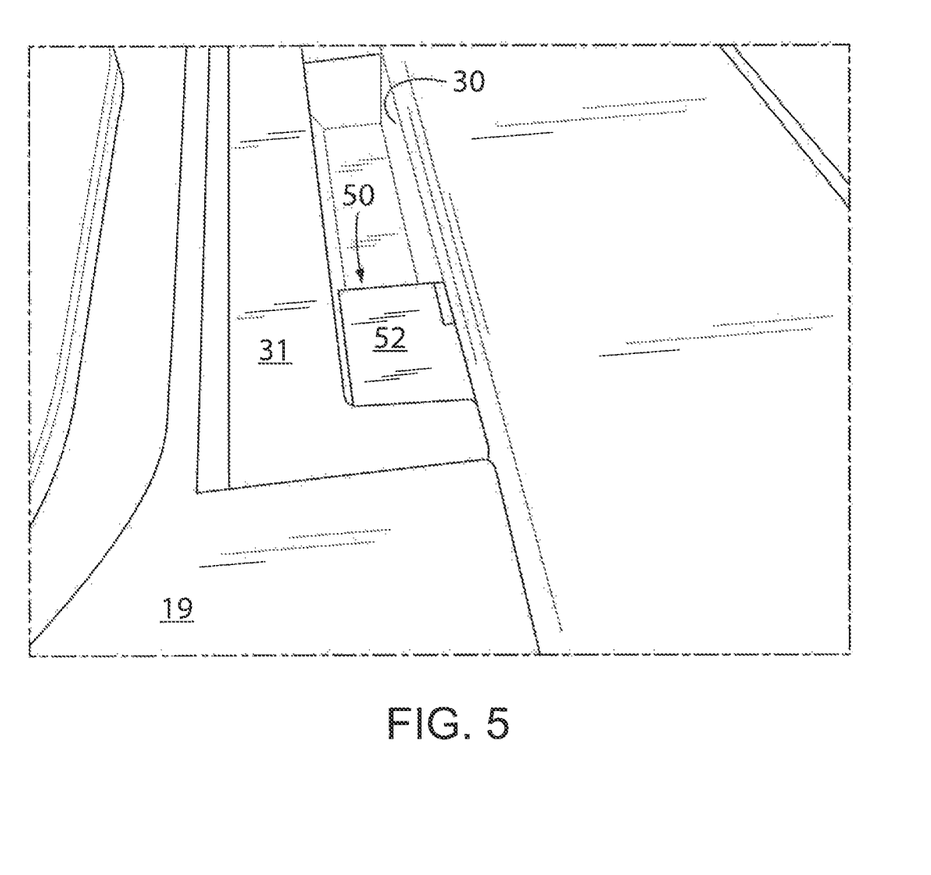
FIG. 5 is a pictorial view of the set of pneumatic ports on the scan table of the MRI scanner of FIG. 2 with one embodiment of a pneumatic to wireless audio signal conversion device connected taken from the top and left side.

With reference also to FIGS. 3-5, the table 16 may include a chamber 30 in which a set of pneumatic ports are provided to facilitate connection of pneumatic devices. According to the illustrated embodiment, a first port 32 within the chamber 30 is an audio interface port through which the receiver 18 transmits the pneumatic audio signals. A second port 34 within the chamber 30 provides a connection for a vacuum cushion. A first pneumatic tube 41 for a vacuum cushion includes a plug end 43 that may be inserted into the second port 34 and tubing 45 that runs from the plug end 43 to the vacuum cushion. A third port 36 within the chamber 30 provides a connection for a squeeze bulb. A second pneumatic tube 40 for the squeeze bulb includes a plug end 42 that may be inserted into the third port 36 and tubing 44 that runs from the plug end 42 to the squeeze bulb. It is contemplated that a portion of the above described ports may be removed from or still additional pneumatic ports may be included within the chamber 30 without deviating from the scope of the invention.

Traditionally, a pneumatic headset is plugged into the first port 32 to deliver the pneumatic audio signals to a patient. However, the pneumatic headset requires pneumatic tubing of sufficient length to extend from the first port 32 to the head of a patient. A patient may initially be positioned for imaging on a sliding top 19 of the table 16 external to the bore 14 of the scanner 12. The sliding top 19 is then inserted into the bore for imaging. Consequently, if the chamber 30 is located on a fixed region of the table 16, the pneumatic tubing must be able to extend not only from the first port 32 to the head of the patient but also for the distance of the sliding top 19 as the patient is inserted into the bore 14 of the scanner 12. Patients may also require additional medical equipment during imaging. For instance, sensors monitoring physiological conditions such as heart rate, blood oxygen levels, cardiac electrical signals, respiration and the like may be provided. Other equipment such as a respirator may also be necessary. Each of the devices requires wiring or connections between the patient and the device. The number of wires and/or tubes may decrease patient comfort or risk entanglement. Thus, it would be desirable to deliver the pneumatic audio signal without using the pneumatic tubing.

Figure 11:
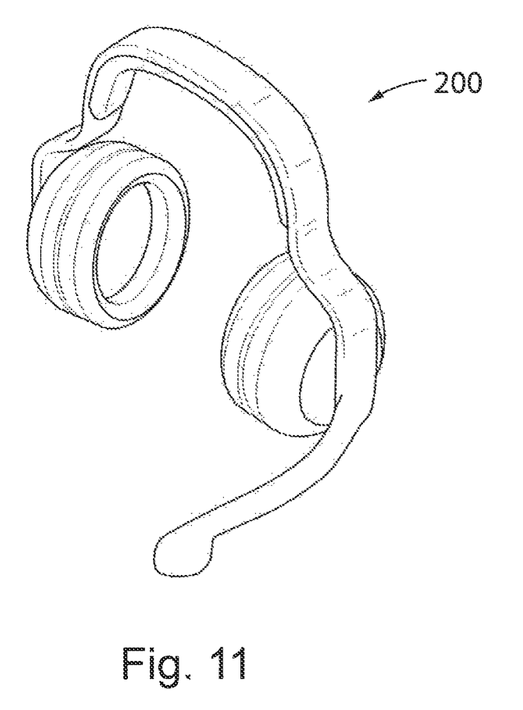
FIG. 11 is an exemplary wireless headset that may be used in cooperation with the pneumatic to wireless audio signal conversion device.
Figure 12:
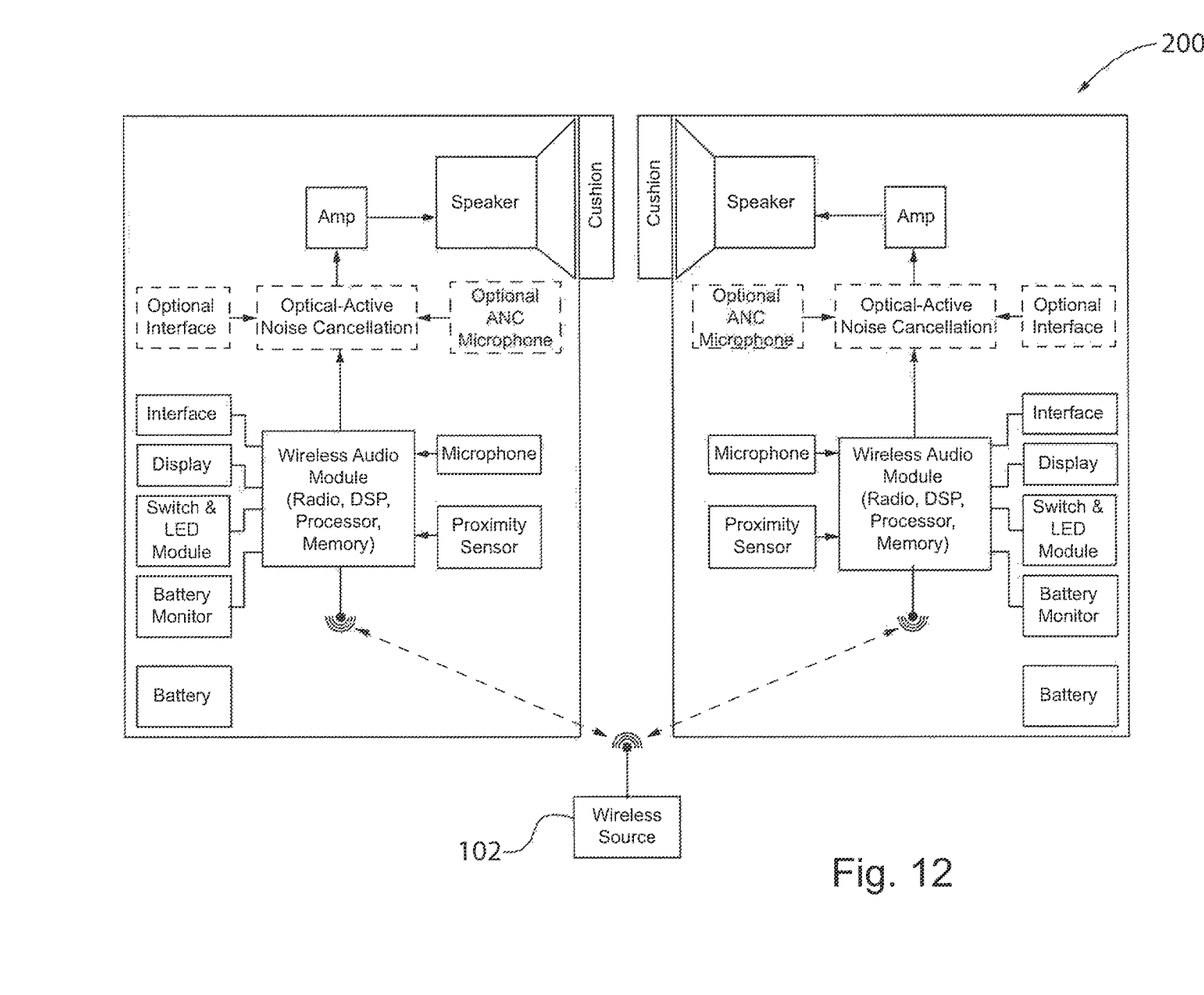
FIG. 12 is a block diagram representation of the wireless headset of FIG. 11.

Referring next to FIGS. 6-10, one embodiment of a pneumatic audio signal to wireless audio signal converter 50 is illustrated. The converter 50 is inserted into the first port 32 to receive the pneumatic audio signals. The converter 50 generates wireless audio signals responsive to the pneumatic audio signals which are then transmitted to a wireless receiver in a wireless audio delivery system, such as a wireless headset 200, worn by the patient (see also FIGS. 11-12). The converter 50 and wireless headset 200 transmit the audio signal form the audio port 32 to the headset 200 without using pneumatic tubing.

The illustrated converter 50 includes a housing 60 formed from an upper housing 61 and a lower housing 63. The upper and lower housings 61, 63 are secured together via a set of screws 65 extending through an opening 67 in the upper housing 61 and engaging a threaded receptacle 69 in the lower housing 63. The screws 65 also pass through openings 102 in a circuit board 100 positioned between the upper and lower housings to secure the circuit board 100 between the two housings. Although discussed with respect to a particular embodiment, it is understood that the housing 60 may take multiple forms, including, for example, a single molded housing or a housing having more than two portions. Similarly, multiple methods of joining the upper and lower housing 61, 63 to each other may be utilized, such as a boss protruding from one portion and an interlocking tab engaging the boss or a pivotal connection may be formed such that the upper housing 61 opens and closes, rotating about the pivot, without being removed from the lower housing 63. A sealing member 74, such as a gasket, may be included between the upper housing 61 and the lower housing 63. The sealing member may be a foam or rubber material to provide an airtight seal between the upper housing 61 and the lower housing 63 to reduce infiltration of ambient noise to the interior of the housing 60. These and other embodiments of the housing 60 may be utilized without deviating from the scope of the invention.

The housing 60 also includes a connecting member 70 protruding from one side An upper half 71 of the connecting member 70 is integrally formed with the upper housing 61, and a lower half 73 of the connecting member 70 is integrally formed with the lower housing 63. When the upper and lower housings 61, 63 are joined together, the upper and lower halves 71, 73 of the connecting member 70 form a conical segment protruding from the side of the housing 60. The connecting member 70 is configured to receive a gasket 75 around the outer periphery. According to the illustrated embodiment, the gasket 75 is a segment of tubing 75 which may be elastically deformed to fit around the outer periphery of the connecting member and extend along a portion of the length of the connecting member 70. The size of the tubing 75 and connecting member 70 are configured such that the connecting member 70 and tubing 75 may be inserted into and removed from the audio port 32 in the pneumatic chamber 30. When the connecting member 70 is inserted into the audio port 32, the gasket, or tubing, 75 preferable elastically deforms due to engagement of the audio port 32 creating an airtight seal between the connecting member 70 and the audio port 32. The connecting member 70 includes at least one opening 76 located at the end of the connecting member 70 furthest from the side of the housing 60. According to the illustrated embodiment, three openings 76 extend between a lower and upper edge and are spaced across the distal end of the connecting member 70. The upper and lower halves 71, 73 of the connecting member 70 define a passage 81 extending from an interior of the housing 60 to the opening 76 at the end of the connecting member 70. It is contemplated that the connecting member 70 may have other shapes, such as conical, or with non-circular cross-sections, and be tapered or straight. The connecting member 70 is formed such that it is complementary to the port 32 into which it is to be inserted.

Figure 6:
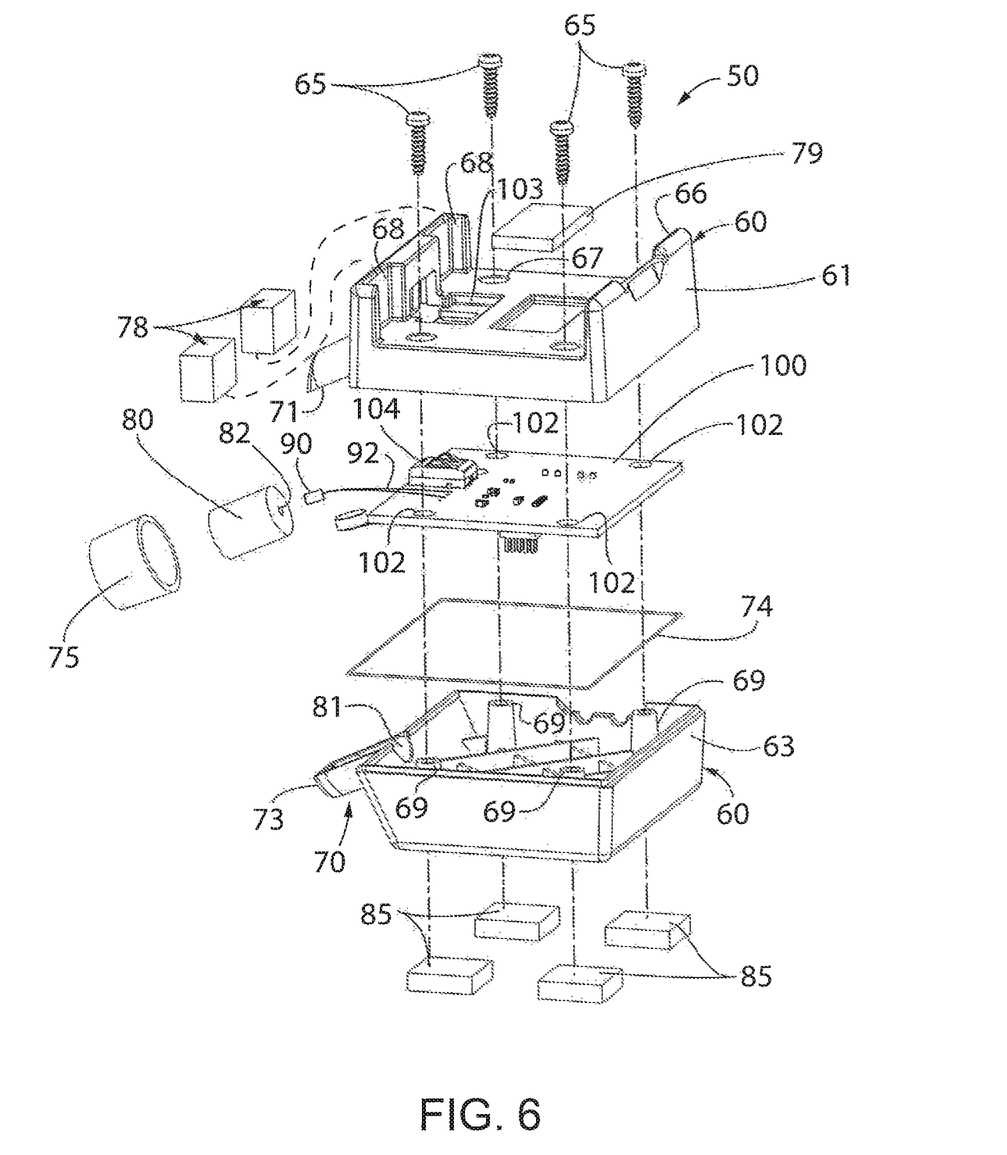
FIG. 6 is an exploded view of the pneumatic to wireless audio signal conversion device of FIG. 5.
Figure 7:
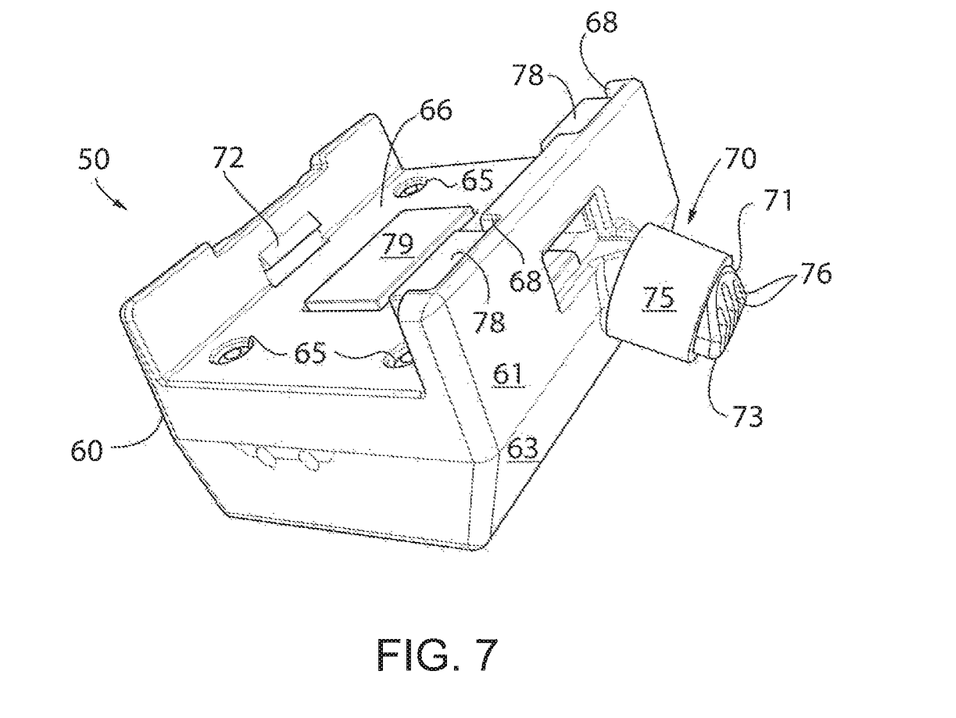
FIG. 7 is a perspective view of the pneumatic to wireless audio signal conversion device of FIG. 5.
Figure 8:
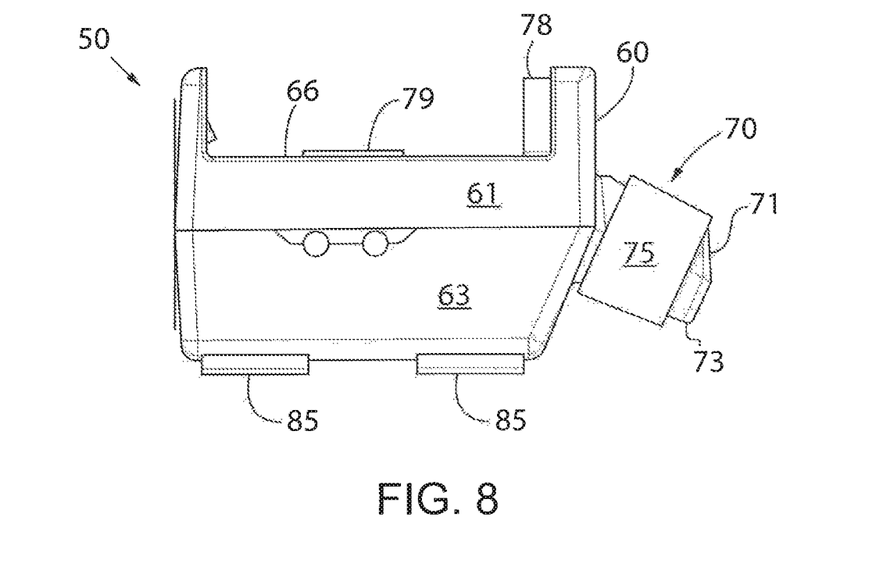
FIG. 8 is a side elevation view of the pneumatic to wireless audio signal conversion device of FIG. 5.
Figure 9:
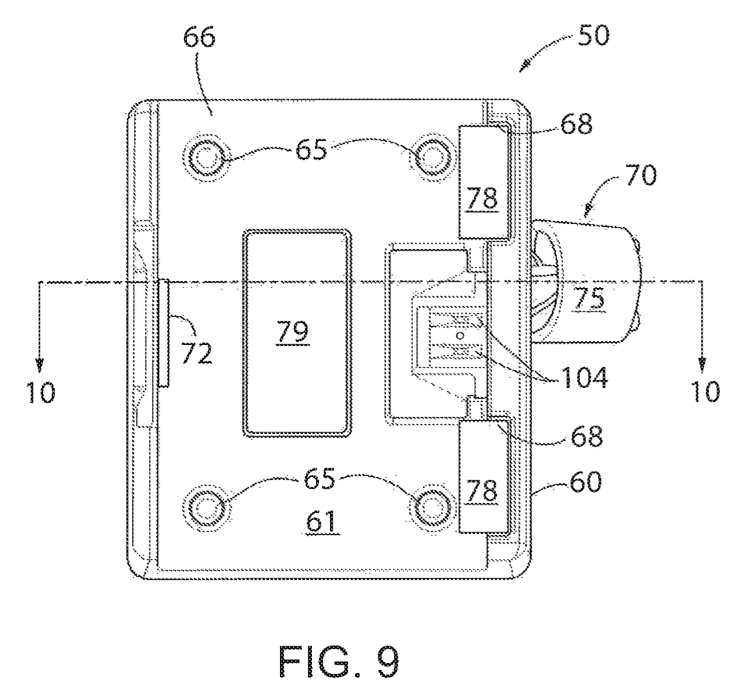
FIG. 9 is a top plan view of the pneumatic to wireless audio signal conversion device of FIG. 5.
Figure 10:
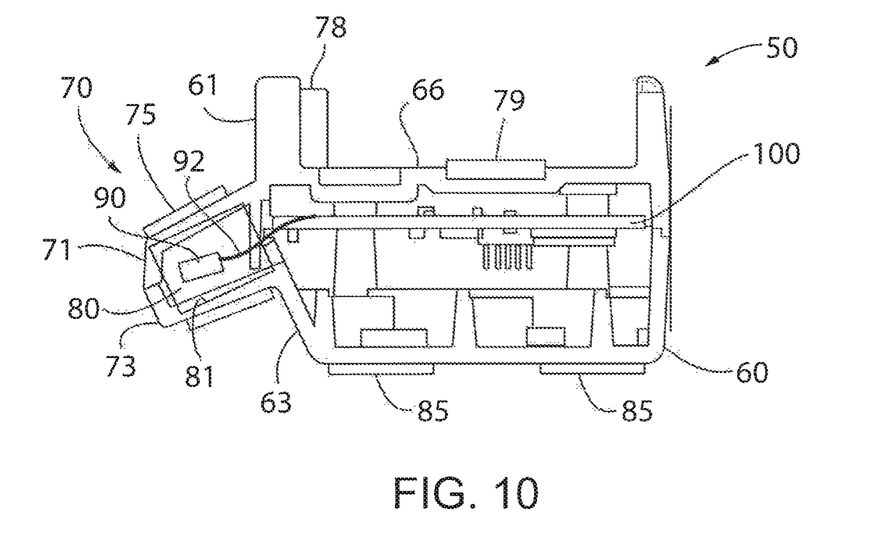

A microphone 90 is inserted into the connecting member 70 to receive the pneumatic audio signals from the pneumatic port 32 and convert them to electronic audio signals which are transmitted via wires 92 to the circuit board 100. The microphone 90 is first inserted into a foam insert 80. The insert 80 includes a channel 82 extending for at least a portion of the length of the insert 80 into which the microphone 90 may be inserted. Optionally, the channel 82 may extend through the entire length of the insert 80. The diameter of the channel 82 is preferably the same size or smaller than the diameter of the microphone 90. When inserted into the channel 82, the microphone is retained by a friction fit and/or causes compression of the foam insert 80 such that the foam insert 80 holds the microphone 90 in place. The foam insert 80 is then located in the connecting member 70. The outer diameter of the foam insert 80 is preferably the same size or larger than the diameter of the inner periphery of the passage 81 in the connecting member 70. As a result, the insert 80 fills the passage 81 in the connecting member 70.

The insert 80 reduces the amount of ambient noise received at the microphone 90 while allowing the pneumatic audio signals from the audio port 32 to reach the microphone 90. The foam surrounding the microphone attenuates the ambient noise that may reach the microphone from directions other than via the channel 82. The channel 82 is directed toward and inserted, at least in part, into the audio port 32 on the MRI scanner 12. The audio signals output from the audio port 32 are received at the microphone 90 through the channel 82 without attenuation resulting from traveling through the foam. Further, the microphone 90 is preferably selected with a low sensitivity such that the microphone detects the pneumatic audio signals from the audio port which are directed toward the microphone with a strong amplitude but does not detect or receives only with a low amplitude ambient audio signals, such as the ambient noise generated by the MRI scanner. In one embodiment, the microphone 90 may be a unidirectional microphone and is positioned in the channel 82 such that the direction from which the unidirectional microphone receives audio signals is oriented toward the audio port 32.

The circuit board 100 includes electronic components to convert the electric audio signals to wireless audio signals. The circuit board 100 may include, for example, a single integrated circuit configured to perform the conversion or separate electronic devices each configured to perform one or more steps of the conversion. Converting the electric audio signal to a wireless audio signal may require functions such as digital signal processing to filter the electric audio signal, an amplifier to vary the level of the signal, and radio frequency modulation of the signal. The wireless audio signal may be formatted according to any suitable wireless communication standard, for example, Bluetooth® or IEEE 802.11. As used herein, a "wireless" signal is a radio frequency (RF) signal transmitted from an RF transmitter to an. RF receiver where the RF transmitter and/or receiver may be discrete electronic components, a portion of an RF transceiver, or a portion of another module, which includes other features, for example processing of the RF signals, and any required supporting electronic circuitry. The circuit board 100 may further include memory to store instructions and a processor operative to execute the stored instructions.

The electronic components are arranged on the circuit board 100 to reduce potential side effects detrimental to either the converter 50 or the MRI scanner. The electronic components are located in close proximity to other components to which they are electrically connected, reducing the length of traces or wire runs between the components, thereby reducing the potential for heating due to currents induced on those traces or wire runs by the MRI scanner. The electronic components are also arranged to minimize the formation of loops, which are susceptible to coupling with the magnetic field from the MRI scanner. Further, electromagnetic shielding may be included on a portion of or on the entire circuit board 100 to reduce the interaction between the MRI scanner and the circuit board 100.

A battery 52 is provided to supply power to the converter 50. The battery 52 is removably connected in a socket 66 integrally formed on the upper housing 61. Foam pads 78 inserted into channels 68 within the socket 66 are compressed by insertion of the battery 52 and help align and retain the battery 52 within the socket 66. Another foam pad 79 is located in the bottom of the socket 66. A clip 72 positively engages the battery 52 to further retain the battery 52 within the socket 66. Electrical contacts on the battery 52 engage battery terminals 104 extending upward from the circuit board 100 through openings 103 in the upper housing 61. The battery 52 is preferably rechargeable and may be removed for charging and inserted for use. The battery 52 supplies power to the circuit board 100 for operation of the electronic components mounted thereto. Thus, the converter 50 does not need to obtain power from the scanner 12. Foot pads 85 may be provided on the bottom of the lower housing 63 to stabilize the converter 50 within the pneumatic chamber 30.

The battery 52 is also susceptible to electromagnetic interference. When the MRI scanner 12 is used, eddy currents are induced in the batteries creating two undesired phenomena: unwanted time-varying gradients and shifts in the main magnetic field (Bo). To reduce electromagnetic interference, the battery 52 may use a non-ferrous battery, such as one or more lithium polymer batteries. The electromagnetic interference within the batteries may also be reduced by using multiple batteries having a smaller capacity rather than a single battery. The eddy currents induced in each battery circulate within the battery and have smaller amplitudes than eddy currents induced in a single large battery. Thus, the effects of the eddy currents are reduced by creating multiple smaller eddy currents instead of one large eddy current.

Each of the components of the converter 50 is constructed of materials having low magnetic susceptibility and low magnetic signature. Magnetic susceptibility is a physical property of materials which identifies to what degree the material is affected by an applied magnetic field. If a material has high magnetic susceptibility, it is affected more significantly by an applied magnetic field, becoming magnetized itself and being attracted to the source of the applied magnetic field. If the applied magnetic field is strong enough and the material has a sufficiently high magnetic susceptibility, an object may be drawn toward the source of the applied magnetic field. Conversely, materials with low magnetic susceptibility are relatively unaffected by an applied magnetic field. These materials either do not become magnetized or are magnetized in such a minor degree as they will not be drawn toward the source of the applied magnetic field and will not distort the homogeneity of the scanner's applied magnetic field. As is understood in the art, MRI scanners generate magnetic fields having uniform field density and having a field strength ranging, for example, from 0.5-3 Tesla. As used herein, a material having low magnetic susceptibility will not be drawn toward the magnetic field generated by the scanner. A material having a low magnetic signature will not distort the uniform field to a degree that it would create an artifact in an MRI image.

Further, the converter 50 is configured to minimize undesired RF emissions at frequencies that may interfere with the scanner 12. Frequencies similar to the MRI frequencies would interfere with the MRI scanner, causing noise and zipper artifacts that interfere with the MRI signal. MRI scanners 12 commonly operate at 64 MHz and 128 MHz. Thus, the converter 50 may utilize shielding to reduce RF emissions at and below 128 MHz. Further, the converter 50 may be configured to generate RF audio signals for transmission at a frequency well above the 128 MHz, such as 2.4 or 2.5 GHz, In operation, the converter 50 receives pneumatic audio signals from a pneumatic audio port 32 and generates wireless audio signals to deliver the audio content to a patient. A controller 20 for an MRI scanner 12 may include equipment to provide audio content to a patient. For example, the controller 20 may have a microphone into which a technician speaks or a library of audio files that may be played back to the patient during a procedure. The controller 20 may further include interconnections to a pneumatic receiver which receives the audio signals and converts the audio signals to pneumatic audio signals for delivery to the patient. The converter 50 receives these pneumatic audio signals and delivers them wirelessly to the patient. Thus, the converter 50 eliminates the need for an expensive and complex installation of wireless communication equipment with existing scanner audio connections, and there is no need to modify or connect to existing scanner wiring.

The connecting member 70 on the converter 50 is plugged into an existing audio port, such as the audio port 32 for pneumatic headphones located on the scan table 16. Optionally, a wall-mounted speaker may be present in the scan room for delivering audio content. The connecting member 70 may be plugged into a similar audio port for the wall-mounted speaker or, if no port is present, the connecting member 70 may be positioned proximate the speaker face such that the audible audio signals directly enter the connecting member 70.

The microphone 90 within the connecting member 70 receives the pneumatic audio signals and converts them to electronic audio signals on the circuit board 100 within the converter 50. An RF modulator and antenna are used to transmit the electronic audio signals from the converter 50 to a wireless receiver. An exemplary wireless receiver is described, for example, in U.S. Pat. No. 9,264,793 and U.S. Pat. No. 9,438,981, both entitled MRI Compatible Headset and co-owned by the Applicant of this application, the contents of which are incorporated herein by reference. The converter 50 may serve as the wireless source described in the '793 and '981 patents.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. An audio signal converter for use in a magnetic resonance imaging (MRI) environment, comprising:
   a housing;
   a connecting member extending from the housing, wherein:
   the connecting member has an outer periphery that is complementary to a pneumatic audio port within the MRI environment,
   the connecting member is operative to be inserted into the pneumatic audio port,
   the connecting member includes an opening at an end distal from the housing, and
   a passage extends through the connecting member from the opening to an interior of the housing;
   a microphone mounted proximate the connecting member and operative to receive a pneumatic audio signal via the passage in the connecting member and to convert the pneumatic audio signal to an electronic audio signal; and
   a wireless transmitter mounted within the housing, wherein the wireless transmitter is operative to receive the electronic audio signal and to transmit a radio frequency (RF) audio signal to a receiver within the MRI environment, wherein each of the components of the audio signal converter has a low magnetic susceptibility such that the audio signal converter will not be drawn toward a magnetic field applied by an MRI scanner and will not distort the homogeneity of the magnetic field.

2. The audio signal converter of claim 1 wherein the pneumatic audio port is located in a chamber on one of the MRI scanner and a table for the MRI scanner and the housing is configured to fit in the chamber on the MRI scanner or the table for the MRI scanner.

3. The audio signal converter of claim 1 further comprising an insert configured to be fitted within the passage of the connecting member, the insert including a first end and a second end, wherein:
   the first end is proximate the interior of the housing when the insert is fitted within the passage of the connecting member,
   the insert, includes a channel extending from the first end for at least a portion of a length of the insert, and
   the microphone is configured to be positioned within the channel of the insert.

4. The audio signal converter of claim 1 further comprising a gasket mounted to the outer periphery of the connecting member and operative to form a seal between the outer periphery of the connecting member and the pneumatic audio port when the connecting member is inserted into the pneumatic audio port.

5. The audio signal converter of claim 1 wherein the housing includes at least two portions, the audio signal converter further comprising a sealing member included between the two portions when the two portions are joined together to form the housing.

6. The audio signal converter of claim 1 wherein the microphone is a low sensitivity microphone.

7. The audio signal converter of claim 1 wherein the pneumatic audio port is a speaker within the MRI environment and the connecting member is operative to be positioned proximate the speaker generating an audio signal for a patient in the MRI environment.

8. The audio signal converter of claim 1 further comprising a rechargeable battery pack, wherein the rechargeable battery pack includes a plurality of batteries.

9. A method for converting pneumatic audio signals to radio frequency (RF) wireless signals in a magnetic resonance imaging (MRI) environment, the method comprising the steps of:

inserting a connecting member of an audio signal converter into a pneumatic audio port located in the MRI environment;

receiving an audio signal with a microphone in the audio signal converter from the pneumatic audio port via a passage extending through the connecting member in the audio signal converter;

converting the audio signal to an electronic audio signal with the microphone; and converting the electronic audio signal to an RF wireless signal with a wireless transmitter mounted in the audio signal converter. Wherein each of the components of the audio signal converter has a low magnetic susceptibility such that the audio signal converter will not be drawn toward a magnetic field applied by an MRI scanner and will not distort the homogeneity of the magnetic field.

10. The method of claim 9 wherein the pneumatic audio port is located in a chamber on one of the MRI scanner and a table for the MRI scanner and the housing is configured to fit in the chamber on the MRI scanner or the table for the MRI scanner.

11. The method of claim 9 further comprising the step of attenuating an ambient noise received at the microphone wherein the ambient noise is generated by operation of the MRI scanner.

12. The method of claim 11 wherein:

the audio signal converter includes an insert configured to be fit within the passage of the connecting member, the insert includes a channel extending from a first end for at least a portion of a length of the insert, the microphone is configured to be positioned within the channel of the insert, the audio signal converter further includes a gasket mounted to the outer periphery of the connecting member and operative to form a seal between the outer periphery of the connecting member and the pneumatic audio port when the connecting member is inserted into the pneumatic audio port, and the insert and the gasket are operative to attenuate the ambient noise generated by the MRI scanner.

13. A system for delivering pneumatic audio signals to a patient in a magnetic resonance imaging (MRI) scanner, the system comprising:

a signal converter, including:

a housing;

a connecting member extending from the housing, wherein:

the connecting member has an outer periphery that is complementary to a pneumatic audio port on one of the MRI scanner and a table for the MRI scanner, the connecting member is operative to be inserted into the pneumatic audio port, the connecting member includes an opening at an end distal from the housing, and a passage extends through the connecting member from the opening to an interior of the housing;

a microphone mounted proximate the connecting member and operative to receive a pneumatic audio signal via the passage in the connecting member and to convert the pneumatic audio signal to an electronic audio signal; and a wireless transmitter mounted within the housing, wherein the wireless transmitter is operative to receive the electronic audio signal and to transmit a radio frequency (RF) audio signal to a receiver within the MRI environment; and a wireless audio delivery system, including:

the receiver operative to receive the RF audio signal and to convert the RF audio signal to a second electronic audio signal within the wireless headset, and at least one speaker operative to convert the second electronic audio signal to an audible audio signal proximate an ear of the patient, wherein each of the components of the signal converter and of the wireless headset has a low magnetic susceptibility such that the signal converter and the wireless headset will not be drawn toward a magnetic field applied by an MRI scanner and will not distort the homogeneity of the magnetic field.

14. The system of claim 13 wherein:

the signal converter further includes an insert configured to be fitted within the passage of the connecting member, the insert including a first end and a second end, the first end is proximate the interior of the housing when the insert is fitted within the passage of the connecting member, the insert includes a channel extending from the first end for at least a portion of a length of the insert, and the microphone is configured to be positioned within the channel of the insert.

15. The system of claim 13 wherein the audio signal converter further includes a gasket mounted to the outer periphery of the connecting member and operative to form a seal between the outer periphery of the connecting member and the pneumatic audio port when the connecting member is inserted into the pneumatic audio port.

16. The system of claim 13 wherein the housing of the signal converter includes at least two portions, and the signal converter further includes a sealing member included between the two portions when the two portions are joined together to form the housing.

17. The system of claim 13 wherein the microphone is a low sensitivity microphone.

18. The system of claim 13 wherein the connecting member is operative to be positioned proximate a speaker generating an audio signal for the patient in the MRI scanner.

19. The system of claim 13 wherein the signal converter further includes a rechargeable battery pack, wherein the rechargeable battery pack includes a plurality of batteries.

* * * * *